United States Patent
Butler

(10) Patent No.: US 6,936,743 B2
(45) Date of Patent: Aug. 30, 2005

(54) METHOD FOR EXTENDING CATALYST LIFE IN PROCESSES FOR PREPARING VINYL AROMATIC HYDROCARBONS

(75) Inventor: James R. Butler, Webster, TX (US)

(73) Assignee: Fina Technology, Inc., Houston, TX (US)

( * ) Notice: Subject to any disclaimer, the term of this patent is extended or adjusted under 35 U.S.C. 154(b) by 160 days.

(21) Appl. No.: 10/235,279

(22) Filed: Sep. 5, 2002

(65) Prior Publication Data

US 2004/0049091 A1 Mar. 11, 2004

(51) Int. Cl.$^7$ .............................................. C07C 5/333
(52) U.S. Cl. ...................................... 585/444; 585/440
(58) Field of Search ................................. 585/444, 440

(56) References Cited

U.S. PATENT DOCUMENTS

| | | | | |
|---|---|---|---|---|
| 4,590,324 A | * | 5/1986 | Satek | 585/444 |
| 5,503,163 A |  | 4/1996 | Boyd | 128/849 |
| 5,689,023 A |  | 11/1997 | Hamilton, Jr. | 585/444 |
| 5,689,027 A | * | 11/1997 | Abichandani et al. | 585/481 |
| 5,739,071 A | * | 4/1998 | Chen et al. | 502/53 |
| 6,184,174 B1 |  | 2/2001 | Rubini et al. | 502/304 |

OTHER PUBLICATIONS http://www.cheresources.com/polystymonzz.shtml; *Styrene Monomer Production (Dow Process).*

* cited by examiner

*Primary Examiner*—Thuan D Dang
(74) *Attorney, Agent, or Firm*—Madan Mossman & Sriram; Tenley R. Krueger

(57) ABSTRACT

Disclosed is a method for extending the life of dehydrogenation catalysts used to prepare vinyl aromatic hydrocarbons. The catalysts, which typically include both iron oxide and potassium containing catalysis promoter, are exposed to additional potassium delivered using a potassium carboxylate. The potassium carboxylates are desirably free of halogens and other catalysts poisons or groups that could result in the undesirable properties in vinyl aromatic hydrocarbons produced therewith. The present invention is particularly useful with the production of styrene and methyl styrene.

12 Claims, No Drawings

METHOD FOR EXTENDING CATALYST LIFE IN PROCESSES FOR PREPARING VINYL AROMATIC HYDROCARBONS

BACKGROUND OF THE INVENTION

1. Field of the Invention

The present invention relates to a method for extending the life of dehydrogenation catalysts. The present invention particularly relates to a method for extending the life of catalysts used to dehydrogenate alkyl aromatic hydrocarbons to form vinyl aromatic hydrocarbons.

2. Background of the Art

Vinyl benzenes play a particularly important role in the preparation of synthetic plastics and resins. The polymerization of styrenes, for example, to produce polystyrene resins is well known.

Styrene and styrene derivatives are typically produced from ethylbenzene materials by dehydrogenation over solid catalysts in the presence of steam. Catalysts found to be effective and useful for this process include those based on potassium oxide promoted, chromium oxide stabilized, iron oxide materials as disclosed in, for example, U.S. Pat. No. 5,503,163 to Chu. Another catalyst reported to be useful for preparing styrene from ethylbenzene is itself prepared from extruded alpha-FeOOH iron oxide particles derived from scrap metal via dehydration of a yellow alpha-Fe(OOH) intermediate via the Penniman process and devoid of bound sulfate, having a median size of at least 2 microns. These catalysts, as disclosed in U.S. Pat. No. 5,689,023 to Hamilton, Jr., also are prepared from a formulation that includes a potassium containing compound. U.S. Pat. No. 6,184,174 B1 to Rubini, et al., discloses catalysts for dehydrogenating ethylbenzene to styrene which comprise iron oxide, oxides of alkaline and alkaline-earth metals, oxides of the lanthanide series, oxides of metals of the sixth group, prepared from a paste of iron oxide impregnated with an aqueous solution of a cerium salt, treated with aqueous KOH and calcined, after drying, to pre-form potassium ferrate, to which the other components or precursors of the catalyst are then added.

A typical process for preparing styrene is the so-called "Dow Process." As reported in "The Chemical Engineers' Resource Page" at http://www.cheresources.com/polystymonzz.shtml, in the DOW Process, the energy needed for the conversion of ethylbenzene to styrene is supplied by superheated steam at about 720° C. that is injected into a vertically mounted fixed bed catalytic reactor with vaporized ethylbenzene. The catalyst is iron oxide based and contains $Cr_2O_3$ and a potassium compound, KOH or $K_2CO_3$, which act as reaction promoters. Typically, 0.7–2.0 kg of steam is required for each kilogram of ethylbenzene to ensure sufficiently high temperatures throughout the reactor. The superheated steam supplies the necessary reaction temperature of 550–670° C. throughout the reactor.

After the conversion reaction, the products are cooled rapidly to prevent polymerization. The product stream, containing styrene, toluene, benzene, and unreacted ethylbenzene, is fractionally condensed after the hydrogen is flashed from the stream. After adding a polymerization inhibitor, the styrene is vacuum distilled in a series of four columns, often times packed columns, to 99.8% purity. Typical capacity per plant ranges from 200,000 to 400,000 metric tons per year in each reactor and most plants contain multiple reactors or units.

While processes such as the Dow Process are useful for preparing commercial quantities of styrene and other vinyl aromatic hydrocarbons, these process are not without problems. One major problem is loss of catalyst activity. As with most reactions using catalysts wherein the catalyst is retained within the process, the catalyst may, with time, lose reactivity and selectivity. Simply replacing aged catalysts is usually not an economically viable resolution of this problem. The above-described catalysts are expensive to make and replacing the catalyst usually requires that the operating unit be shut down. Any loss of production time is always undesirable and excessive maintenance can greatly increase the cost of producing vinyl aromatic hydrocarbons, such as styrene. It would be desirable in the art of producing vinyl aromatic hydrocarbons to extend the life of catalysts used in vinyl aromatic hydrocarbon production.

SUMMARY OF THE INVENTION

In one embodiment, the present invention is an improvement to a method for preparing a vinyl aromatic hydrocarbon from a feed stream, the feed stream including an alkyl aromatic hydrocarbon. These methods, as described above, include at least the steps of feeding an alkyl aromatic hydrocarbon to a catalyst bed to dehydrogenate the feed to form a mixture from which the vinyl aromatic hydrocarbons are separated. The improvement of the present invention includes supplying a catalyst life extender to at least one reaction chamber loaded with a dehydrogenation catalyst used to prepare the vinyl aromatic hydrocarbon from the feed stream wherein the dehydrogenation catalyst includes an iron oxide catalyst and an alkali metal catalysis promoter and the catalyst life extender is a potassium salt of a carboxylic acid.

DETAILED DESCRIPTION OF INVENTION

In one embodiment, the present invention is an improvement in a process to prepare a vinyl aromatic hydrocarbon prepared by dehydrogenating an alkyl aromatic hydrocarbon wherein the dehydrogenation is performed using a dehydrogenation catalyst. The present invention is particularly useful with processes wherein the catalyst is one containing iron and at least one alkali metal compound, typically potassium, acting as a catalysis promoter. Such dehydrogenation catalysts are well known in the art and some of those that are available commercially include: the S6-20, S6-21 and S6-30 series from BASF Corporation; the C-105, C-015, C-025, C-035, and the FLEXICAT series from CRI Catalyst Company, L.P.; and the G-64, G-84 and STYROMAX series from Sud Chemie, Inc.

The catalysts listed above can typically contain from about 40 to about 80 percent $Fe_2O_3$, from about 5 percent to about 30 percent $K_2O$, and other catalysis promoters. While these are typical catalysts used in processes that can benefit from the method of the present invention, the method of the present invention can be used with any process to prepare vinyl aromatic hydrocarbons wherein the life of the catalyst or catalysts for that process can be extended by supplying an alkali metal compound to the reaction chamber containing the catalyst.

It is known to provide potassium to a process for preparing a vinyl aromatic hydrocarbon. For example, U.S. Pat. No. 5,739,071 to Chen, et al., incorporated herein by reference, discloses regenerating and/or stabilizing the activity of a dehydrogenation catalyst used in dehydrogenating an alkyl aromatic hydrocarbon to obtain an alkenyl aromatic hydrocarbon, the method comprising the steps of continuously or intermittently adding to a reactant stream an effective amount of an alkali metal or alkali metal compound without interrupting the dehydrogenation reaction. What is not disclosed therein is the improvement of using an alkali metal compound that is neither deliquescent like potassium carbonate and potassium hydroxide nor dangerously reactive like potassium metal.

The method of the present invention can be used in connection with the catalytic dehydrogenation of virtually any alkyl aromatic hydrocarbon to a corresponding vinyl aromatic hydrocarbon. The appropriate combination of alkyl aromatic hydrocarbon, catalyst and reaction conditions in order to obtain a particular desired vinyl aromatic hydrocarbon is generally well known in the art and, in any event, would be a matter of choice and routine experimentation. The method of this invention is of particular utility in connection with extending the life of a dehydrogenation catalyst used in a process of converting ethylbenzene to styrene. It is also useful in the production of methyl styrene. The method of the present invention can be used with any such process subject to the process preferably having the minimum elements of: using a dehydrogenation catalyst that can have its useful life extended by being exposed to potassium, and having a feed stream to a bed of such a catalyst that includes or can at least tolerate sufficient steam to supply the catalyst life extender at a level sufficient to maintain catalyst activity and selectivity for an extended period of time.

In the practice of the method of the present invention, a catalyst life extender is supplied to at least one reaction chamber used to prepare the vinyl aromatic hydrocarbon. The catalyst life extender is a compound containing potassium and is neither excessively deliquescent nor dangerously reactive, and has a melting point or vapor point such that it can be used at normal process temperatures without blocking lines or fouling process equipment. Preferably, the catalyst life extender is a potassium salt of a carboxylic acid. More preferably, the catalyst life extender is selected from the group including the potassium salts of mono-carboxylic acids having from 2 to about 10 carbons. Most preferably, the catalyst life extender is potassium acetate.

The potassium carboxylates useful as the catalyst life extenders of the method of the present invention are substantially free of any catalysts poisons. For example, it has been reported that halogen ions, such as chloride, have typically been found to poison dehydrogenation catalysts. The potassium carboxylates of the present invention have little or no halogen substituents. Similarly, they are also free of any atoms or groups that could impart undesirable properties to the vinyl aromatic hydrocarbons produced using the method of the present invention.

The potassium carboxylates useful with the present invention are preferably vaporous under process conditions within the processes wherein they are used. The potassium carboxylates are injected using steam as a source of heat and vaporization. It is important that the potassium carboxylates be sufficiently stable that the potassium carboxylates, or at least their stable potassium bearing decomposition products, function to deliver potassium to the dehydration catalysts.

The catalyst life extenders of the present invention can be used to provide an effective amount of potassium to dehydrogenation catalysts, sufficient to maintain the dehydrogenation catalyst at substantially constant levels of catalyst activity and selectivity. Using the process of the present invention, the dehydrogenation catalyst can be maintained at near original conversion and selectivity activity for months and even years. The ability to maintain such catalyst activity levels is very advantageous for a commercial process as it reduces down time with a resultant increase in production and lowers maintenance expenses.

While the selection of the specific catalyst life extender, the catalyst being maintained, and the particular vinyl aromatic hydrocarbon being produced may affect the level of catalyst life extender fed into a process, preferably, the catalyst life extender is supplied at a rate equivalent to a continuous addition of from about 0.01 to about 100 parts per million by weight of catalyst life extender relative to the weight of the total alkyl aromatic hydrocarbon directed into the reactor. More preferably, the catalyst life extender is supplied at a rate equivalent to a continuous addition of from about 0.10 to about 10 parts per million by weight of catalyst life extender relative to the weight of the total alkyl aromatic hydrocarbon directed into the reactor. Most preferably, the catalyst life extender is supplied at a rate equivalent to a continuous addition of about 5 parts per million by weight of catalyst life extender relative to the weight of the total alkyl aromatic hydrocarbon directed into the reactor.

Preferably, the method of the present invention is used with a process for preparing a vinyl aromatic hydrocarbon that already includes steam in the process. For example, the DOW process uses steam as a heat source and is a process with which the method of the present invention is useful. A solution of the catalyst life extender in water or alcohol can be pumped into the process as needed.

In an alternative embodiment, the catalyst life extenders of the present invention are introduced into a vinyl aromatic hydrocarbon process by continuously injecting the catalyst life extender directly into the process feed stream. The catalyst life extenders can also be introduced directly into the catalyst bed, but generally this is not a preferred means of employing the method of the present invention as it can result in uneven distribution of the catalyst life extender and care should be taken to ensure that the entire catalyst bed is exposed to the catalyst life extenders. Any means or method of introducing the catalyst life extenders to the catalyst bed of a vinyl aromatic hydrocarbon process known to those of ordinary skill in the art can be used with the method of the present invention.

Just as the catalysts life extenders can be introduced into a process for preparing a vinyl aromatic hydrocarbon by more that one means, it is also within the scope of the present invention to introduce the catalyst life extenders at more than one rate. For example, and preferably, the catalyst life extenders can be introduced continuously. In the alternative, the catalyst life extenders can be introduced periodically when catalyst activity levels fall below a predetermined point. In still another embodiment, the catalyst life extenders can be added at a relatively low level continuously, but additional catalyst life extender can be spiked into the process when catalyst activity levels fall below a predetermined point.

In the method of the present invention, a catalyst life extender is introduced into a process for preparing a vinyl aromatic hydrocarbon. Such processes are typically run at a temperature of from about 300° C. to about 800° C. The catalyst life extender of the present invention can be selected to be at least molten and preferably vaporous at all points in the process upstream of the catalyst bed. For example, potassium acetate, a preferred catalyst life extender of the present invention has a melting point of 292° C. and can be used with most processes for preparing styrene and other vinyl aromatic hydrocarbons.

What is claimed is:

1. A method for preparing a vinyl aromatic hydrocarbon from a feed stream, the feed stream including an alkyl aromatic hydrocarbon, comprising supplying a catalyst life extender to at least one reaction chamber loaded with a dehydrogenation catalyst used to prepare the vinyl aromatic hydrocarbon from the feed stream, wherein the dehydrogenation catalyst includes an iron oxide catalyst and a KOH promoter and the catalyst life extender is potassium acetate.

2. The method of claim 1 further comprising supplying the catalyst life extender to the at least one reactor at a rate equivalent to a continuous addition of from about 0.01 to about 100 parts per million by weight of catalyst life extender relative to the weight of the total alkyl aromatic hydrocarbon directed into the reactor.

3. The method of claim 2 further comprising supplying the catalyst life extender to the at least one reactor at a rate equivalent to a continuous addition of from about 0.10 to about 10 parts per million by weight of catalyst life extender relative to the weight of the total alkyl aromatic hydrocarbon directed into the reactor.

4. The method of claim 3 further comprising supplying the catalyst life extender to the at least one reactor at a rate equivalent to a continuous addition of 5 parts per million by weight of catalyst life extender relative to the weight of the total alkyl aromatic hydrocarbon directed into the reactor.

5. The method of claim 1 further comprising supplying the catalyst life extender to the at least one reaction chamber without interrupting the preparation of the vinyl aromatic hydrocarbon.

6. The method of claim 1 wherein steam is already present in the feed stream.

7. The method of claim 1 additionally comprising adding steam to the feed stream.

8. The method of claim 7 additionally comprising using the steam to inject the catalyst life extender into the feed stream.

9. The method of claim 1 additionally comprising injecting the catalyst life extender directly into the feed stream.

10. The method of claim 1 additionally comprising delivering the catalyst life extender directly to the catalyst bed.

11. The method of claim 1 wherein the method is performed at a temperature of from about 300° C. to about 800° C.

12. The method of claim 1 wherein the vinyl aromatic hydrocarbon is styrene or methyl styrene.

* * * * *